(12) United States Patent
Walraevens et al.

(10) Patent No.: US 9,999,770 B2
(45) Date of Patent: Jun. 19, 2018

(54) COCHLEAR IMPLANT ELECTRODE ARRAY INCLUDING RECEPTOR AND SENSOR

(71) Applicants: Cochlear Limited, Macquarie University, NSW (AU); Universität Zürich, Zürich (CH)

(72) Inventors: Joris Walraevens, Mechelen (BE); Pieter Wiskerke, Antwerp (BE); Francesca Paris, Mechelen (BE); Alexander Huber, Zurich (CH); Lukas Prochazka, Zurich (CH); Dominik Obrist, Zurich (CH)

(73) Assignees: Cochlear Limited, Macquarie University, NSW (AU); Universität Zürich, Zürich (CH)

( * ) Notice: Subject to any disclaimer, the term of this patent is extended or adjusted under 35 U.S.C. 154(b) by 249 days.

(21) Appl. No.: 14/534,733

(22) Filed: Nov. 6, 2014

(65) Prior Publication Data

US 2015/0126900 A1 May 7, 2015

Related U.S. Application Data

(60) Provisional application No. 61/901,272, filed on Nov. 7, 2013.

(51) Int. Cl.
*A61N 1/36* (2006.01)
*A61B 5/12* (2006.01)
(Continued)

(52) U.S. Cl.
CPC .......... *A61N 1/36032* (2013.01); *A61B 5/125* (2013.01); *A61B 5/4836* (2013.01); *A61N 1/0541* (2013.01); *A61N 1/36036* (2017.08); *A61N 1/36135* (2013.01); *A61B 5/686* (2013.01); *A61B 2562/028* (2013.01); *A61B 2562/0247* (2013.01)

(58) Field of Classification Search
CPC ..... A61B 5/03; A61N 1/0541; A61N 1/36032
See application file for complete search history.

(56) References Cited

U.S. PATENT DOCUMENTS 5,782,744 A 7/1998 Money
6,259,951 B1 7/2001 Kuzma et al.
(Continued)

FOREIGN PATENT DOCUMENTS

DE 10 2009 058 414 A1 2/2011
WO 97/18689 A1 5/1997
(Continued)

OTHER PUBLICATIONS

International Search Report and Written Opinion for International Application No. PCT/IB2014/065881 dated Jan. 29, 2015.
(Continued)

*Primary Examiner* — Christopher D Koharski
*Assistant Examiner* — Natasha Patel
(74) *Attorney, Agent, or Firm* — Pilloff & Passino LLP; Martin J. Cosenza

(57) ABSTRACT

A device including a cochlear implant electrode array and an apparatus configured to sense a phenomenon of fluid in a cochlea, wherein the apparatus and the electrode array are a single unit.

26 Claims, 17 Drawing Sheets

(51) Int. Cl.
  *A61N 1/05* (2006.01)
  *A61B 5/00* (2006.01)

(56) References Cited

U.S. PATENT DOCUMENTS

| | | |
|---|---|---|
| 6,473,651 B1 | 10/2002 | Kuzma et al. |
| 7,394,909 B1 | 7/2008 | Widmer et al. |
| 7,580,754 B2 | 8/2009 | Zhang et al. |
| 8,128,551 B2 | 3/2012 | Jolly |
| 9,173,024 B2 * | 10/2015 | Bolognia ............... H04R 3/002 |
| 2002/0071585 A1 | 6/2002 | Miller |
| 2004/0200281 A1 | 10/2004 | Kenny et al. |
| 2005/0101832 A1 | 5/2005 | Miller et al. |
| 2005/0197524 A1 | 9/2005 | Miller et al. |
| 2005/0245990 A1 | 11/2005 | Roberson |
| 2006/0107744 A1 | 5/2006 | Li et al. |
| 2007/0282396 A1 * | 12/2007 | Overstreet ......... A61N 1/36032 607/57 |
| 2011/0112355 A1 | 5/2011 | Van Den Heuvel |
| 2011/0245714 A1 * | 10/2011 | Volckaerts ......... A61N 1/36032 600/559 |

FOREIGN PATENT DOCUMENTS

| | | |
|---|---|---|
| WO | 99/031933 A1 | 6/1999 |
| WO | 2011/066295 A1 | 6/2011 |

OTHER PUBLICATIONS

Extended European Search Report for EP Patent No. 3 065 669, dated May 11, 2017.

\* cited by examiner

COCHLEAR IMPLANT ELECTRODE ARRAY INCLUDING RECEPTOR AND SENSOR

CROSS-REFERENCE TO RELATED APPLICATIONS

This application claims priority to Provisional U.S. Patent Application No. 61/901,272, entitled Cochlear Implant Electrode Array Including Receptor and Sensor, filed on Nov. 7, 2013, naming Joris WALRAEVENS and others as inventors, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In an exemplary embodiment, there is a device, comprising: a cochlear implant electrode array; and an apparatus configured to sense phenomenon of fluid in a cochlea, wherein the apparatus and the electrode array are a single unit.

In another exemplary embodiment, there is a prosthesis, comprising an intra-cochlear sub-section including a pressure receptor; and a middle-ear cavity sub-section including a pressure sensor in pressure communication with the pressure receptor.

In another exemplary embodiment, there is a prosthesis, comprising a physical phenomenon receptor and a sensor remote from the receptor, wherein the prosthesis is configured such that the physical phenomenon received by the receptor is communicated without transduction to the sensor.

In another exemplary embodiment there is a method comprising receiving a signal from a pressure sensitive transducer, the transducer being located at least substantially immediately proximate to the base of a cochlea outside the cochlea, and applying electric stimulation from a cochlear implant electrode array to the cochlea based on the signal from the pressure sensitive transducer, wherein the signal is indicative of a change in a physical property of fluid inside the cochlea.

In another exemplary embodiment there is a method comprising sensing a change in a physical property of fluid inside a cochlea from outside the cochlea utilizing an apparatus that includes a MEMS sensor positioned inside the middle ear of the recipient, and evoking a hearing percept based on the sensed change.

BRIEF DESCRIPTION OF THE DRAWINGS

Embodiments of the present invention are described below with reference to the attached drawings, in which.

DETAILED DESCRIPTION

Figure 1A:
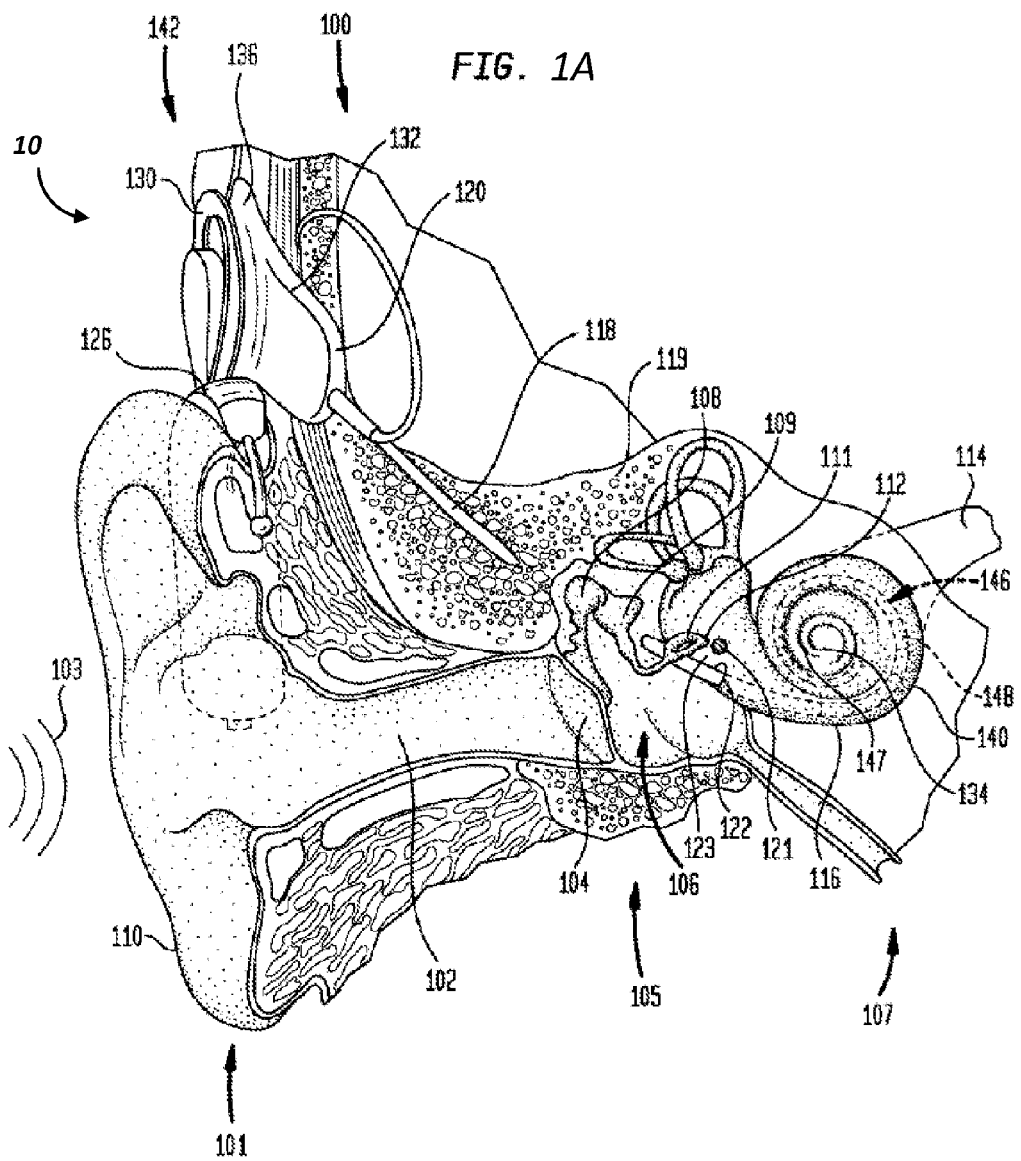
FIG. 1A is a perspective view of an exemplary hearing prosthesis utilized in some exemplary embodiments.

FIG. 1A is perspective view of a totally implantable cochlear implant, referred to as cochlear implant 100, implanted in a recipient. The totally implantable cochlear implant 100 is part of a system 10 that can include external components, as will be detailed below.

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant.

In the illustrative arrangement of FIG. 1A, external device 142 may comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which may be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In embodiments of the present invention, internal energy transfer assembly 132 and main implantable component 120 are hermetically sealed within a biocompatible housing. In embodiments of the present invention, main implantable component 120 includes a sound processing unit (not shown) to convert the sound signals received by the implantable microphone in internal energy transfer assembly 132 to data signals. Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

As noted, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source may comprise, for example, a rechargeable battery. During operation of cochlear implant 100, the power stored by the power source is distributed to the various other implanted components as needed. The power source may be located in main implantable component 120, or disposed in a separate implanted location.

It is noted that the teachings detailed herein and/or variations thereof can be utilized with a non-totally implantable prosthesis. That is, in an alternate embodiment of the cochlear implant 100, the cochlear implant 100 is traditional hearing prosthesis.

While various aspects of the present invention are described with reference to a cochlear implant, it will be understood that various aspects of the embodiments detailed herein are equally applicable to other stimulating medical devices having an array of electrical simulating electrodes such as auditory brain implant (ABI), functional electrical stimulation (FES), spinal cord stimulation (SCS), penetrating ABI electrodes (PABI), and so on. Further, it should be appreciated that the present invention is applicable to stimulating medical devices having electrical stimulating electrodes of all types such as straight electrodes, peri-modiolar electrodes and short/basilar electrodes. Also, various aspects of the embodiments detailed herein and/or variations thereof are applicable to devices that are non-stimulating and/or have functionality different from stimulating tissue, such as for, example, any intra-body dynamic phenomenon (e.g., pressure, or other phenomenon consistent with the teachings detailed herein) measurement/sensing, etc., which can include use of these teachings to sense or otherwise detect a phenomenon at a location other than the cochlea (e.g., within a cavity containing the brain, the heart, etc.).

Figure 1B:
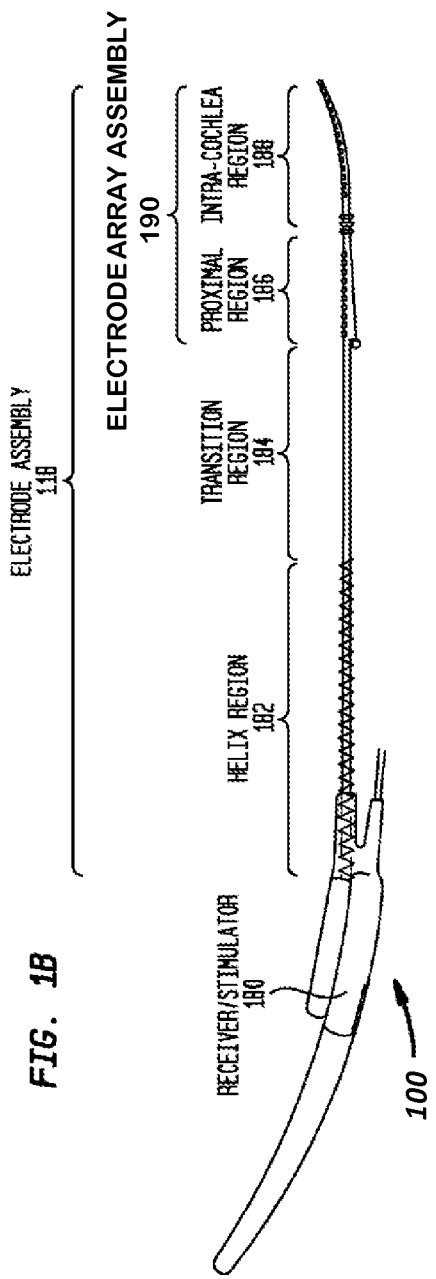
FIG. 1B is a side view of the implantable components of the cochlear implant illustrated in FIG. 1A.

FIG. 1B is a side view of a cochlear implant 100 without the other components of system 10 (e.g., the external components). Cochlear implant 100 comprises a receiver/stimulator 180 and an electrode assembly or lead 118. Electrode assembly 118 includes a helix region 182, a transition region 184, a proximal region 186, and an intra-cochlear region 188. Proximal region 186 and intra-cochlear region 188 form an electrode array assembly 190. In an exemplary embodiment, proximal region 186 is located in the middle-ear cavity of the recipient after implantation of the intra-cochlear region 188 into the cochlea. Thus, proximal region 186 corresponds to a middle-ear cavity sub-section of the electrode array assembly 190. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected through lead 118 to receiver/stimulator 180, through which respective stimulating electrical signals for each electrode contact 148 travel.

Figure 2:
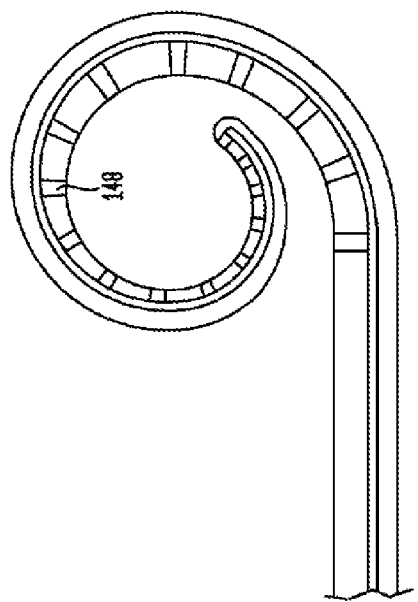
FIG. 2 is a side view of an embodiment of the electrode array illustrated in FIGS. 1A and 1B in a curled orientation.
Figure 3A:
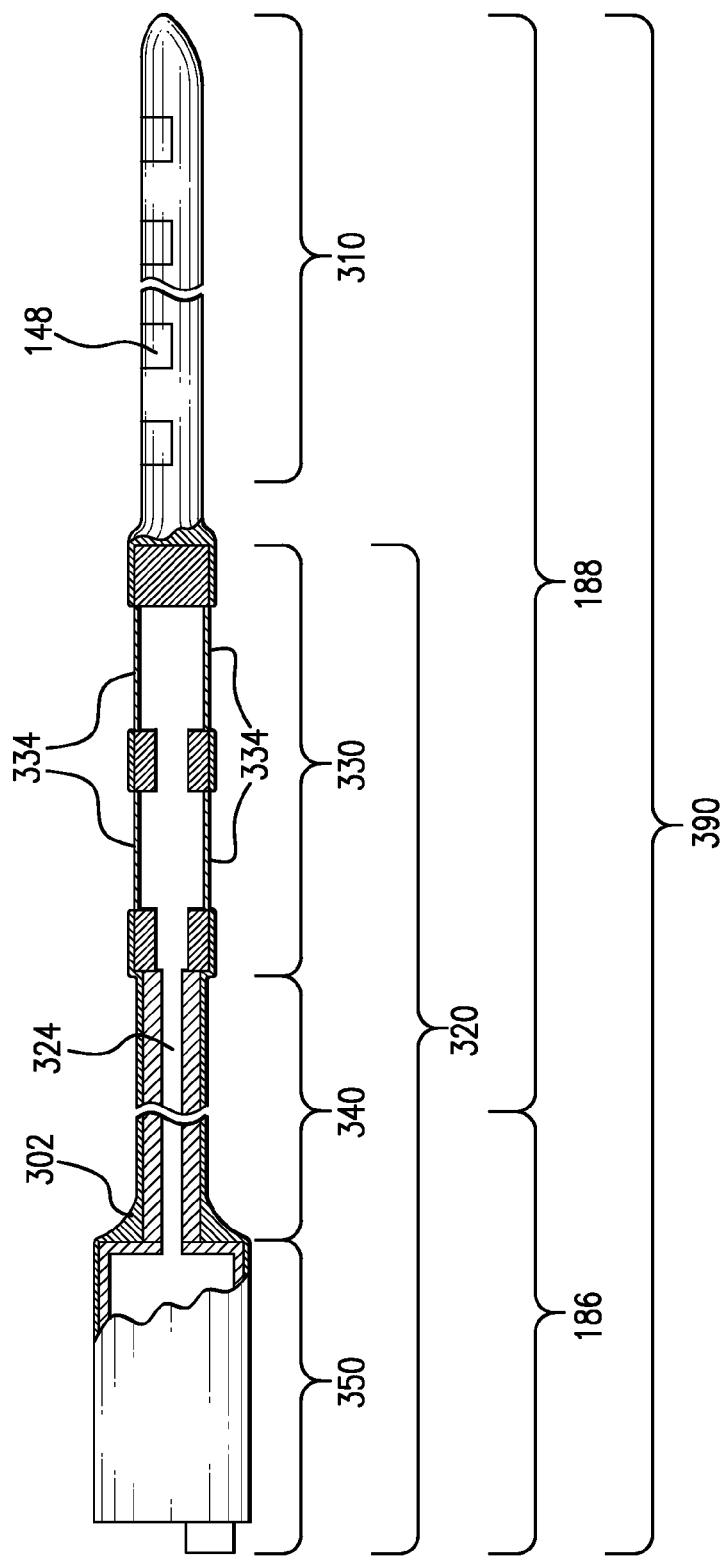
FIG. 3A is a side view of an exemplary electrode array assembly according to an embodiment.

FIG. 2 is a side view of electrode array assembly 190 in a curled orientation, as it would be when in situ in a patient's cochlea, with electrode contacts 148 located on the inside of the curve. FIG. 3A shows the electrode array of FIG. 2 in situ in a patient's cochlea 140.

FIG. 3A depicts a side view of a device 390 corresponding to a cochlear implant electrode array assembly that can include some or all of the features of electrode array assembly 190 of FIG. 1B. More specifically, in an exemplary embodiment, electrode assembly 118 includes electrode array assembly 390 instead of electrode array assembly 190 (i.e., 190 is replaced with 390). Thus, according to an exemplary embodiment, there is a cochlear implant 100 as detailed above which includes electrode array assembly 390, where the electrodes of the electrode array assembly 390 are in communication with the remaining portions of the implantable component of the cochlear implant in a conventional manner (albeit the leads or the like are potentially rerouted about the electrode array assembly 390 in order to accommodate the teachings detailed herein and/or variations thereof). Additional details of electrode array assembly 390 will now be provided.

Electrode array assembly 390 includes a cochlear implant electrode array 310 and an apparatus 320 configured to sense a phenomenon of the fluid in a cochlea. In an exemplary embodiment, electrode array assembly 390 has some and/or all of the functionality of electrode array assembly 190, where electrode array assembly 190 corresponds to a state-of-the-art electrode array assembly and/or variations thereof and/or an earlier model electrode array assembly. By way of example only and not by way of limitation, electrode array assembly 390 includes any electrode array 310 comprising a plurality of electrodes 148. The electrode array assembly 390 is configured such that the electrodes 148 of the electrode array 310 are in and/or can be placed in signal communication with the receiver stimulator 180.

In some embodiments, the phenomenon sensed by the apparatus 320 is a pressure of the fluid in the cochlea and/or a change in pressure of the fluid in the cochlea. In an exemplary embodiment of FIG. 3A, the apparatus 320 is a pressure sensor assembly. Along these lines, in an exemplary embodiment, by way of example only and not by way of limitation, the apparatus 320 has the exemplary functionality of sensing pressure and/or pressure variations in fluid in the cochlea caused by vibrations impinging upon the outside of the cochlea and transmitted therein (e.g., through the oval window via ossicular vibrations (natural and/or prosthetically based), through the round window in scenarios where for whatever reason the round window transfers vibrations into the cochlea, and/or through any other part of the cochlea such that the cochlear fluid vibrates in a manner that the teachings detailed herein and/or variations thereof can be practiced). In at least some exemplary scenarios, the vibrations that impinge upon the outside of the cochlea and are transmitted therein are vibrations based on an ambient sound that would otherwise ultimately evoke a hearing percept in a normal hearing person. Accordingly, in an exemplary embodiment, the apparatus 320 is configured to utilize one or more phenomena of fluid in the cochlea associated with normal hearing and output a signal indicative of that phenomenon, where the outputted signal is based on ambient sound that caused or otherwise resulted in the one or more phenomena.

Figure 3B:
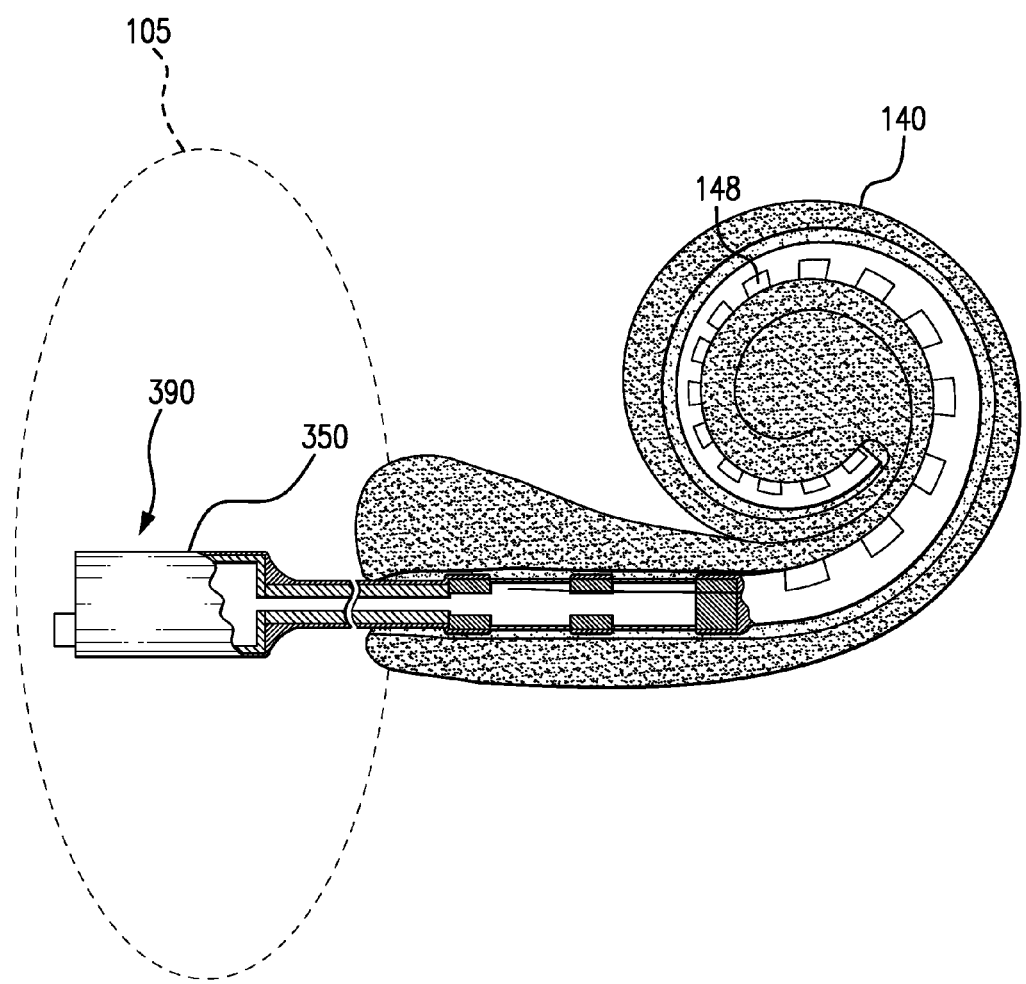
FIG. 3B is a conceptual side view of the exemplary electrode array of FIG. 3A inserted into a cochlea.

More particularly, apparatus 320 includes a physical phenomenon receptor 330 which is in fluid communication with conduit 340 which is in turn is in fluid communication with sensor assembly 350. FIG. 3B depicts a conceptual representation of the electrode array assembly 390 inserted into a cochlea 140 that is configured to prosthetically remain in the cochlea (that is it is configured to remain in the cochlea for a time period concomitant with the use of a prosthetic device, as opposed to a temporary insertion such as might be the case for a needle or the like). FIG. 3B depicts a conceptual drawing depicting the intra-cochlea region 188 of the electrode array assembly 390 in the cochlea 140, and the proximal region 186 of the electrode array assembly 390 located outside the cochlea 140, where the conduit 340 of the apparatus 320 extends from inside the cochlea 140 to outside the cochlea into the middle ear cavity, which is functionally represented by the dashed enclosure 105. It is noted that this drawling in FIG. 3B is just that—conceptual, and are provided at least for the purpose of presenting the concept of the cochlear implant electrode array having apparatus 320 that is only partially inserted into the cochlea. In an exemplary embodiment, the electrode array assembly along with the receptor is inserted into the scala tympani. That said, in an alternate embodiment, at least the receptor is inserted into the scala vestibule. Accordingly, in an exemplary embodiment, there is an electrode array assembly configured such that the electrode array is insertable into the scala tympani, and the receptor is insertable into the scala vestibule. In an exemplary embodiment, the entire electrode array assembly is configured to be insertable into the scala vestibule.

Additional details of components of the electrode array assembly 390 will now be described.

Figure 4A:
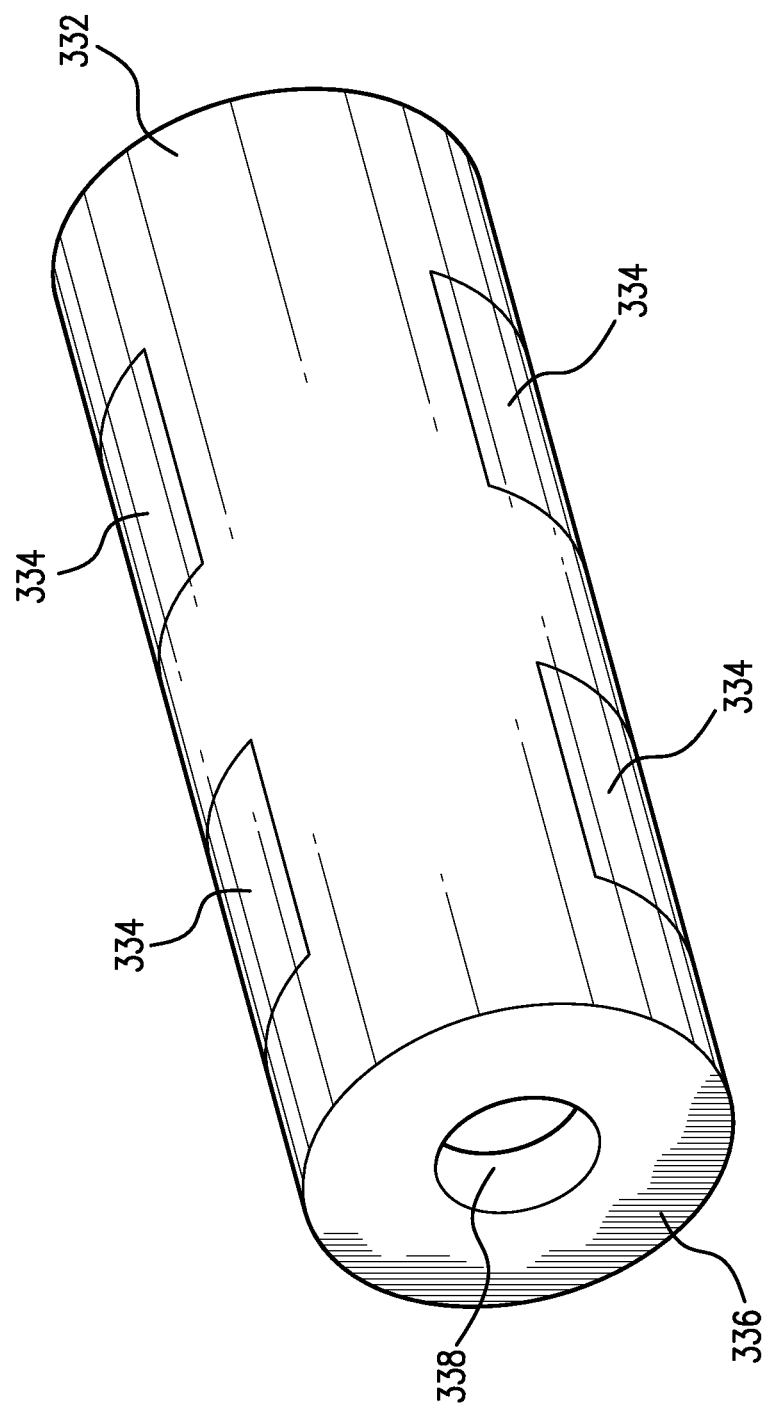
FIG. 4A is an isometric view of a receptor according to an exemplary embodiment.
Figure 4B:
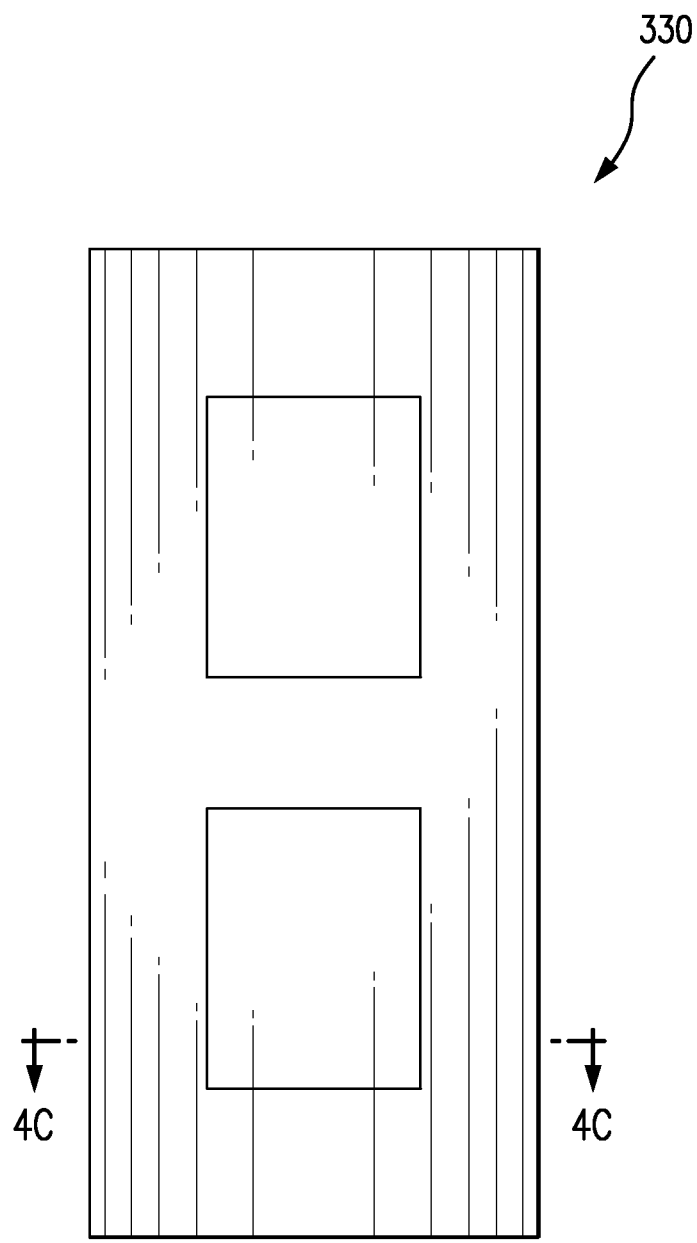
FIG. 4B is a top view of the receptor of FIG. 4A.
Figure 4C:
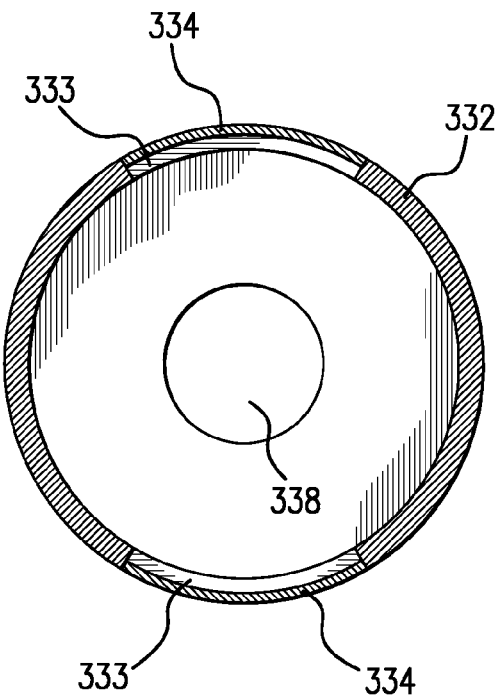
FIGS. 4C and 4D are cross-sectional views of the receptor of FIG. 4A.

FIG. 4A depicts an isometric view of the physical phenomenon receptor 330, FIG. 4B depicts a top view of the receptor 330, and FIG. 4C depicts a cross-section through the receptor 330. All of these views depict the receptor 330 in isolation from other components of the apparatus 320 and the electrode array assembly 390. How the receptor 330 interfaces with these other components is discussed below.

In an exemplary embodiment, the receptor 330 is a pressure receptor. In a non-mutually exclusive fashion, the receptor 330 can be a vibration receptor. As noted above, receptor 330 is a physical phenomenon receptor. Accordingly, in some embodiments, receptor 330 corresponds to any type of receptor that can function as a physical phenomenon receptor providing that the teachings detailed herein and/or variations thereof can be practiced with that receptor.

In the exemplary embodiment of figures, the receptor 330 is a titanium cylinder having a closed end (not shown in FIG. 4A as it is eclipsed by the longitudinal surface of the cylinder) and an end 336 that is open via port 338. Port 338 provides fluid communication between the inside of the cylinder and the outside of the cylinder. Receptor 330 includes four diaphragms 334 arrayed about the longitudinal surface of the cylinder. (The diaphragms are depicted as curved diaphragms, but as detailed below, in alternate embodiments, the diaphragms are flat.) In the embodiments of the figures, the diaphragms 334 cover through holes that extend through the longitudinal surface of the cylinder 332. The diaphragms 334 hermetically seal these holes. The diaphragms 334 configured to deflect or otherwise move as a result of pressure variations and/or vibrations impinging thereupon that are communicated thereto via the cochlea fluid. This causes pressure fluctuations within the receptor 330. In an exemplary embodiment, this is because the deflections of one or more diaphragms 334 change the volume within the receptor 330. Depending on the fluid that fills or otherwise is located in the receptor 330, vibrations can travel through the diaphragms from the cochlea fluid into the fluid inside the receptor 330.

In the embodiment of the figures, there are four separate diaphragms provided with the receptor 330. These diaphragms are evenly spaced laterally about the longitudinal axes of the cylinder 332, as can be seen. Some embodiments can use fewer or more diaphragms. In an exemplary embodiment, one, two, three, four, five, six or more diaphragms can be utilized. Any number of diaphragms that can enable the teachings detailed herein and or variations thereof can be utilized in at least some embodiments.

While a flattened profile of the diaphragms constitutes a rectangle, other shapes can be utilized (e.g. circular, oval, etc.). In an exemplary embodiment, the side length of the diaphragms have a side length of 1.8 mm and a thickness of 7 µm. In an alternate embodiment, the diaphragms correspond to square rectangles, having a side length of about 0.5 mm and a thickness of about 9 µm. In an alternate embodiment, the thickness can be less, (e.g., 0.9 9 µm). Any thickness that can enable the teachings detailed herein and/or variations thereof to be practiced can be utilized in at least some embodiments. It is noted however that diaphragms having alternate dimensions can be utilized (e.g., diaphragms (square or other type of rectangle) having a side length of about 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 mm or any value or range of values therebetween in 0.01 mm increments, 4, 5, 6, 7, 8, 9, 10, 11, 12, 13 or 14 micrometers in thickness, or any value or range of values therebetween in 0.1 micrometer increments, etc.), or 0.4, 0.5, 0.6, 0.7, 0.8, 0.9, 1.0, 1.1, 1.2, 1.3 or 1.4 micrometers in thickness, or any value or range of values therebetween in 0.01 micrometer increments, etc.). Again, any configuration that can enable the teachings detailed herein to be practiced can be utilized in at least some embodiments. Indeed, the aforementioned configurations of diaphragms correspond to those that have been determined to be relatively more readily manufactured than others.

In the embodiments of FIGS. 4A to 4C, the diaphragms 334 are depicted as individual diaphragms. In some exemplary embodiments, these diaphragms can be laser welded to the cylinder 332. Alternatively and/or in addition to this, brazing and/or soldering can be utilized. In an exemplary embodiment, the diaphragm assembly is our utilized, where the diaphragm is held within a frame, which frame is attached to the cylinder 332. Any device system or method that will enable the diaphragms to be attached to the cylinder 332 such that the teachings detailed herein can be practice can be utilized in at least some embodiments. Indeed, along these lines, in an exemplary embodiment, the cylinder 332 comprises four through holes. A single titanium sheet is wrapped around the cylinder 332. A brazing process utilized to adhere the titanium sheet to the cylinder 332. The brazing process adheres the sheet to the portions of the cylinder where there are no holes present. Thus the sheet is free to flex over the holes of the cylinder 332 as a result of pressure changes and/or vibrations. Thus, four diaphragms are obtained from a manufacturing process were only one sheet is utilized.

An alternate embodiment, the diaphragms are manufactured utilizing integrated circuit technology. Accordingly, the diaphragms and/or the receptor assembly correspond to a so-called "passive chip." In an exemplary embodiment, the diaphragms are manufactured utilizing MEMS fabrication technology of modified semiconductor device fabrication technology. Any technology that can be utilized to manufacture diaphragms that can enable the teachings detailed herein and/or variations thereof can be utilized in at least some embodiments.

Figure 4D:
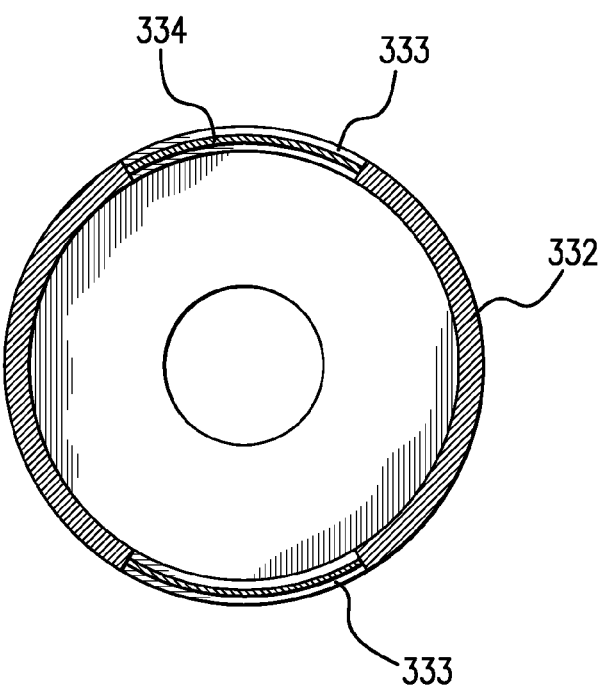

In some alternate embodiments, the diaphragm 334 is located at locations other than the surface of the cylinder 332. For example, FIG. 4D depicts the diaphragms 334 laser welded to the walls forming the through holes 333 cylinder 332. In an exemplary embodiment, the diaphragms can be located with orientations different that that depicted in the figures. For example, one or more or all of the diaphragms can be located at lateral positions relative to the longitudinal axis of the receptor 30 different than that depicted in the figures (e.g., at different angles about the longitudinal axis relative to a lateral axis that extends on the plane in which the electrode array curls. For example, if the diaphragms of the figures are considered to be at angles 0 and 180 degrees relative to the aforementioned lateral axis, diaphragms could be located at plus or minus 15, 30, 45, 60, 75 and/or 90 degrees/plus or minus 195, 210, 225, 240, 255, 270 degrees, etc. Also, in an exemplary embodiment, one or more or all of the diaphragms could be located such that the diaphragm extends normally or at an oblique angle relative to the longitudinal axis.

Figure 4E:
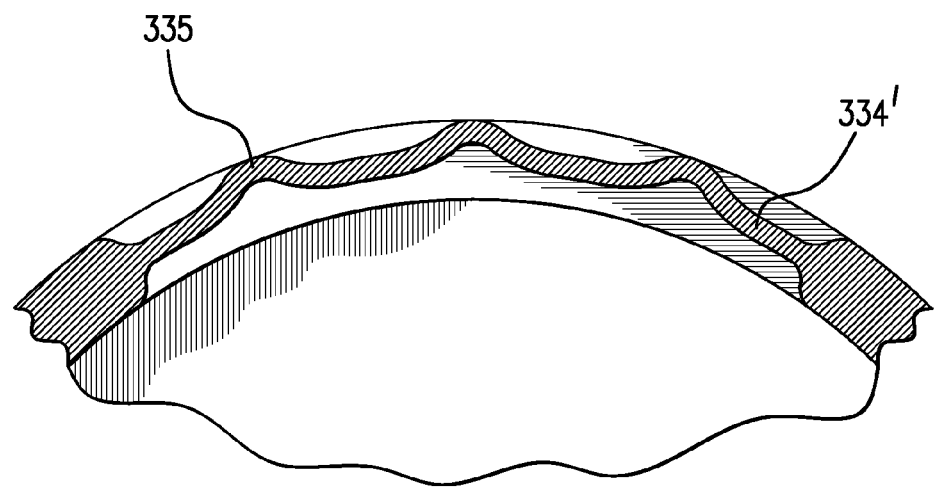
FIG. 4E is a cross-sectional view of an alternate embodiment of the diaphragm.

Referring now to FIG. 4E, there is depicted an alternate embodiment of a diaphragm 334' they can be utilized in the embodiments detailed herein and/or variations thereof, wherein the diaphragm is corrugated. More particularly, FIG. 4C depicts a cross-section through the diaphragm 334', clearly showing corrugations 335. In an exemplary embodiment, the corrugations 335 reduced residuals material stresses in the diaphragm, at least relative to that which would be the case in the absence of the corrugations 335. In an exemplary embodiment, the corrugations can increase the linear relationship between the pressure load and deflection of a "clamped diaphragm" at least relative to that which was the case in the absence of the corrugations 335. It is noted while the corrugations 335 are depicted as being arrayed along one axis of the diaphragm 334', in an alternate embodiment, the corrugations 335 can be arrayed along the opposite axis, and/or can be arrayed in a direction that is oblique to one or both axes. In an exemplary embodiment, the corrugations can run along both axes. Also, while the corrugations depicted in FIG. 4E are shown as zigzag corrugations, in an alternative embodiment, the corrugations can be sine wave corrugations etc. Any configuration of corrugations can be utilized in at least some embodiments providing that the teachings detailed herein and/or variations thereof can be practiced.

Figure 4F:
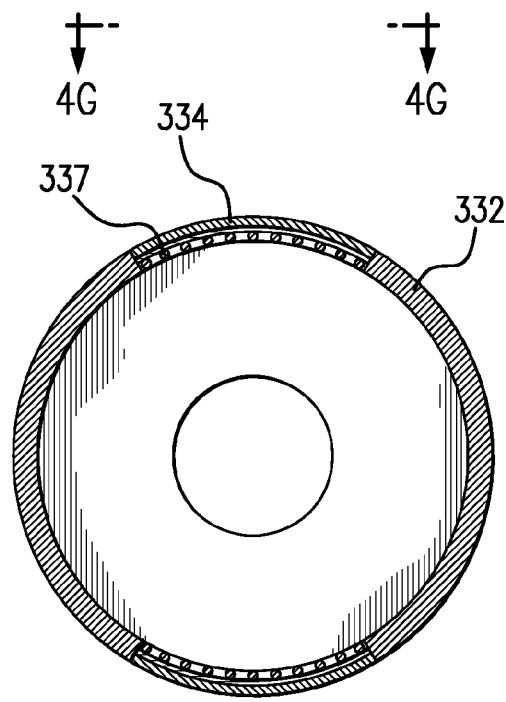
FIGS. 4F and 4G depict views of an exemplary diaphragm. According to an exemplary embodiment.
Figure 4G:
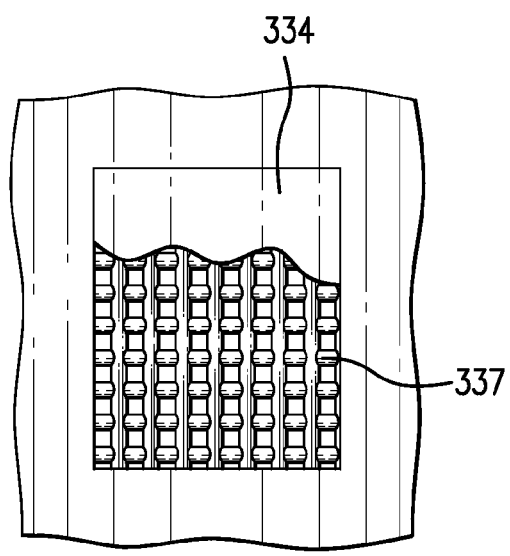

FIG. 4F depicts a cross-sectional view through an alternative embodiment of the receptor 330. This embodiment includes a mechanical stop system 337 for the diaphragm 334, which, in an exemplary embodiment, limits deflection of the diaphragm 334, thereby protecting the diaphragm in some instances (e.g., preventing damage to the diaphragm by preventing excesses deformation thereof). FIG. 4G depicts a portion of this alternate embodiment of the receptor 330 with a portion of the diaphragm 334 for clarity. As can be seen from FIGS. 4F and 4G, the mechanical stop system 337 corresponds to a lattice. The lattice can be formed by beams of circular cross-section, rectangular cross-section, etc. As can be seen, the mechanical stop system 337 is generally contoured to the contour of the diaphragm 334, while being offset from the diaphragm. In alternative embodiments, the lattice can have a flat profile or can have a profile that angles away from the diaphragm (e.g., is curved in an opposite direction from the diaphragm). Also, while a lattice is disclosed in the embodiment of FIGS. 4F and 4G, alternate configurations can be utilized (e.g., a pillar system, where the diaphragm contacts the heads of the pillars in the event of extreme deformation of the diaphragm, thereby limiting further deformation.

Figure 4H:
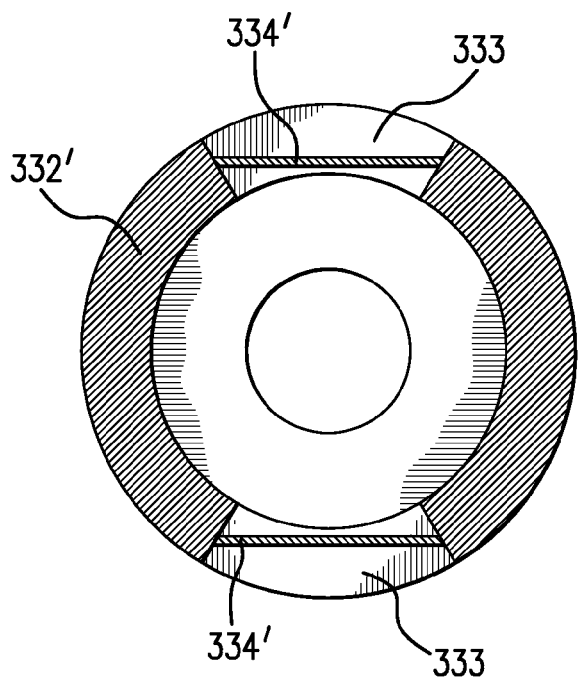
FIGS. 4H and 4I are cross-sectional views of an alternate embodiment of the receptor of FIG. 4A.
Figure 4I:
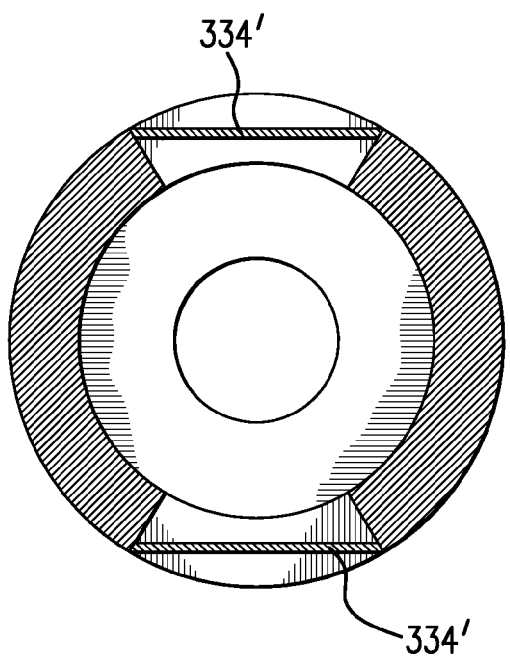

It is noted that while the embodiments depicted in the figures have a diaphragm that is curved, in an alternate embodiment, the diaphragm is flat, as can be seen in FIGS. 4H and 4I, which views correspond to the view of FIG. 4C, except having a flat diaphragm 334'. As can be seen in FIG. 4H, the diaphragm can be attached to the outer surface of the cylinder 332 (FIG. 4H) or to a side surface of the through-hole 333 (FIG. 4I). While not shown, it can be attached to the inside of the cylinder as well. Any configuration or placement of the diaphragm can be utilized in some embodiments, at least when such configurations or placement enables the teachings detailed herein and/or variations thereof. In embodiments that utilize the diaphragm 334' and also utilize a mechanical stop system, the mechanical stop system can have a flat profile (instead of the contoured lattice (or other structure having a holistic contour), the contour is flat) and can have a contour that is in the opposite direction. In this regard, any mechanical stop system configuration that can protect the diaphragm from damage by limiting the deflection of the diaphragm can be utilized providing that the teachings detailed herein can be practiced.

The embodiment just detailed utilizes titanium as the material of the cylinder 332 and the diaphragms 334. In other embodiments, other materials can be utilized. Also the material of the cylinder 332 can be different than the material of the diaphragms 334. In an exemplary embodiment, silicon-on-insulator wafers can be utilized. For example, such wafers can be coated with a biocompatible material, such as a polyamide or the like. In an exemplary embodiment, the coating is such that any thermal stresses that are introduced do not effectively impact the performance of the wafers/the receptor vis-à-vis utilizing such to accomplish the teachings detailed herein and/or variations thereof. In an exemplary embodiment, a silicon diaphragm, such as, for example, a single crystal silicon diaphragm) is used in place of the titanium diaphragms, and is manufactured using SOI wafers via a micro-fabrication process (e.g., an etching process). This SOI wafer can have three or more layers (silicone layer—corresponding to the device layer, oxide layer—corresponding to a stop layer, and an insulating layer, and, in an exemplary embodiment, there can be a second silicon layer—corresponding to a handle layer).

The diaphragms of the apparatus 320 are configured, in some embodiments, such that the resonant frequency of one or more or all of the diaphragms is equal to and/or greater than about 3, 3.5, 4, 4.5, 5. 5.5, 6, 6.5, 7, 7.5, 8, 8.5, 9, 9.5, 10, 10.5, 11 kHz or more or any value or range of values there between in about 0.1 kHz increments (e.g., about 5.7 kHz, 8.4 kHz, about 5.3 to about 7.7 kHz, etc.). In an exemplary embodiment, the stiffness of one or more or all of the diaphragms is a function of the thickness thereof, where, all other things being equal, increased thickness increases the stiffness of the diaphragm. In an exemplary embodiment, the resonant frequency of one or more or all of the diaphragms is a function of the stiffness, where, all other things being equal, increased stiffness of the diaphragm increases the resonant frequency thereof. It is noted that in an exemplary embodiment, increasing the number of diaphragms increases the sensitivity of the receptor relative to a given resonance frequency of the diaphragms.

In an exemplary embodiment, the sensitivity of the overall apparatus 320 in general, or at least the receptor 330 in particular, is relatively higher with respect to that which would be the case if fewer diaphragms (e.g., one, two or three, etc.) of the configuration detailed above were present. In an exemplary embodiment, the sensitivity of the overall apparatus 320 in general, or at least the receptor 330 in particular, is relatively higher if the compliance of the diaphragm is increased by increasing the diaphragm size and/or by decreasing the diaphragm thickness and/or by using a material with a smaller Young's modulus, relative to that which would be the case in the absence of such.

It is further noted that while the embodiment depicted in the figures utilizes a cylinder 332 as the body of the receptor 330, in an alternative embodiment, a receptor having a different configuration, such as one that has a rectangular cross-section or one that has an oval cross-section can be utilized. Also, while the receptor 330 has been depicted as having a single unitary body (cylinder 332), in an alternative embodiment, two or more bodies can be utilized. In an exemplary embodiment, the separate bodies can be placed in the fluid communication with one another and/or can be fluidly isolated from one another. In an exemplary embodiment, the receptor 330 corresponds to a series of spheres located in series that are in fluid communication with one another. In at least some such exemplary embodiments, owing to the properties associated with at least hemispherical structures, all or substantially part of the spheres can correspond to diaphragm material.

As noted above, receptor 330 includes port 338. In the embodiment of FIG. 3A, conduit 340 is placed into fluid communication with the interior receptor 330 via port 338. In an exemplary embodiment, conduit 340 interfaces with receptor 330 in a male-female relationship, respectively. Alternatively, this relationship can be reversed (i.e. port 338 can have a male portion that extends away from and wall 336, configured to fit inside conduit 340). Any device, system and/or method that can enable conduit 340 to be fixed or otherwise placed in the fluid communication with receptor 330 can be utilized in at least some embodiments.

Conduit 340 extends from receptor 330 to sensor assembly 350, and includes lumen 324 which places the inside of receptor 330 into fluid communication with the sensor assembly 350. In an exemplary embodiment, conduit 340 is a tube. Conduit 340 can be flexible and or rigid. In an exemplary embodiment conduit 340 can be made of titanium. In an exemplary embodiment, in addition to the functionality of placing the receptor into fluid communication with the sensor assembly, conduit 340 has the functionality of maintaining a set/specific/control distance between the sensor assembly 350 (or more accurately, components of the sensor assembly 350 detail below) and the receptor 330. Still further, an exemplary embodiment, conduit 340 provides the transition between the intra-cochlea region 188 and the proximal region 186 of the electrode array assembly 390. In at least some embodiments, while not depicted in the figures, conduit 340 can include other components that have utilitarian value with respect to the tissue-electrode array interface (e.g. ribs, occluding features, antiviral and/or bacterial features etc.).

With respect to the embodiments detailed above, pressure variations and/or vibrations in the cochlea fluid that impinge upon the diaphragms deflect the diaphragms such that pressure fluctuations exist in/vibrations travel thorough the fluid-filled volume (e.g., a gas-filled volume, such as an inert gas such as argon-filled volume, etc.) that corresponds to the interior of the receptor 330 and the conduit 340, as well as the pertinent portions of the sensor assembly 350, in which resides a transducer that converts these pressure fluctuations/vibrations into another form of energy (e.g., electrical signal, an optical signal etc.), which in turn is ultimately provided (directly and/or indirectly) to the receiver stimulator 180 of the cochlear implant 100, which in turn interprets this energy as sound information Some details of the sensor assembly 350 will now be described.

Figure 5:
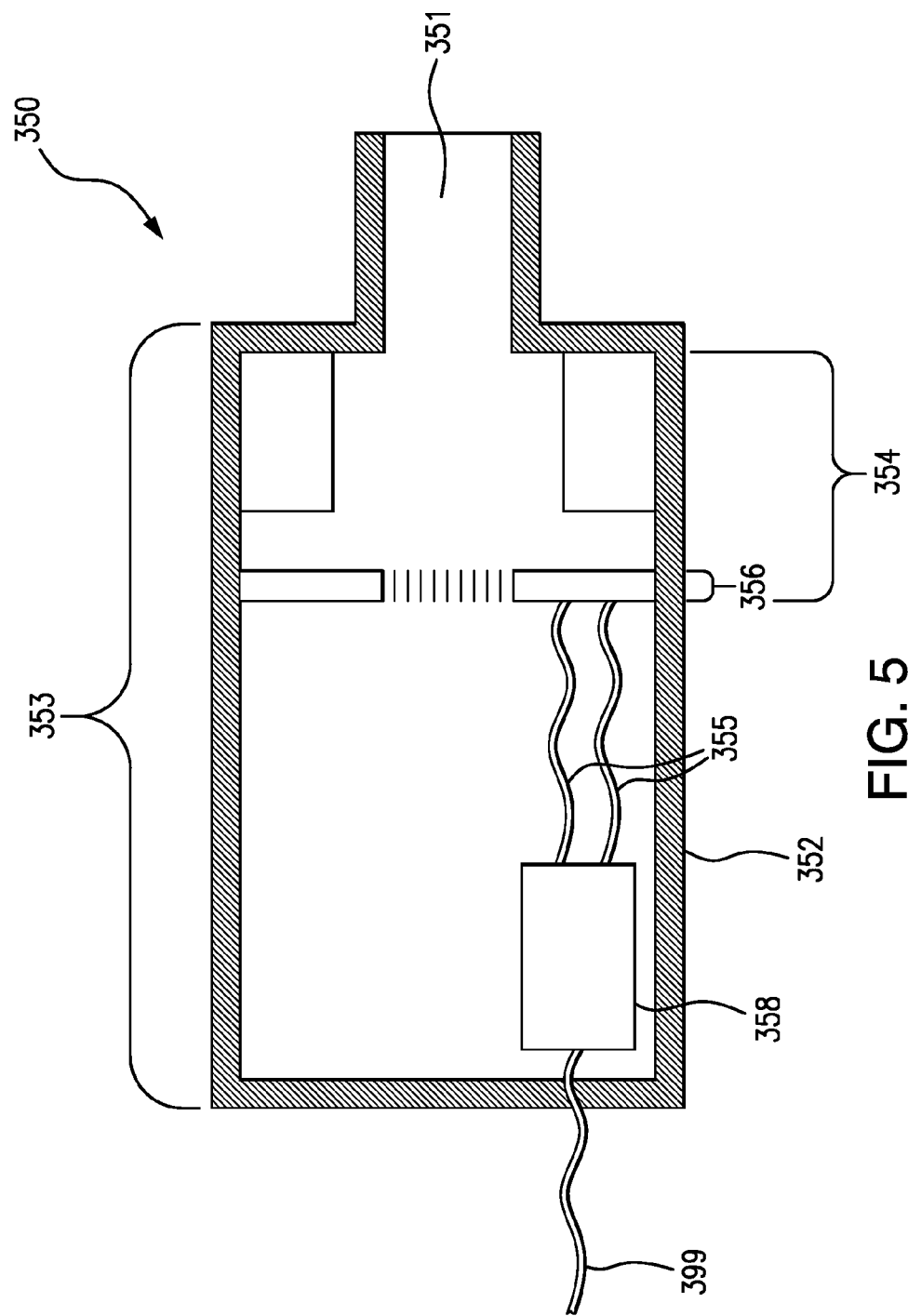
FIG. 5 is a cross-sectional view of the sensor assembly according to an exemplary embodiment.

FIG. 5 depicts a cross-sectional view of the sensor assembly 350 in quasi-black-box format (back lines are not shown for clarity). The sensor assembly 350 includes an enclosed volume 353 established by housing 352 that is fluidly sealed (in some embodiments medically sealed and/or hermetically sealed) with the exception of port 351. As can be seen, port 351 is a male projection from the housing 352 having a hollow interior that is in fluid communication with the interior of the housing 352. In an exemplary embodiment, the male projection interfaces with the conduit 340 in a male—female relationship, respectively. In alternative embodiment, this relationship can be reversed (i.e. port 351 includes only a female portion configured to receive therein conduit 340). Any device, system and/or method that can enable conduit 340 to be fixed or otherwise placed in the fluid communication with sensor assembly 350 can be utilized in at least some embodiments.

Still referring to FIG. 5, housing 352 can be a hollow cylindrical body made of titanium or another biocompatible material. The housing 352 can be made of one or more such materials (e.g. it can be made of entirely titanium and/or a titanium alloy, or can be made out of different materials). The sensor assembly 350 includes a MEMS (micro-electromechanical) condenser microphone 354. The sensor assembly 350 further includes a perforated backplate 356 which in at least some embodiments as part of the microphone 354. In the embodiment of the figures, the microphone 354 is in fluid communication with the lumen 324 of conduit 340, which as noted above is in turn influence communication with the interior of the receptor 330. Thus, in the embodiments of the figures, pressure changes inside the receptor 330 are fluidly communicated to the microphone 354. The microphone 354 includes a pressure-sensitive diaphragm that is etched directly onto a silicon chip. In this regard, the microphone falls within the rubric of "pressure sensor." The pressure changes that occur inside receptor 330 as a result of the pressure changes in the cochlea fluid are sensed by the microphone 354. The microphone outputs the signals via electrical leads 355 to a pre-amplifier 358. The pre-amplifier 358, in at least some embodiments, lowers the noise of the microphone 354 and/or the output impedance of the microphone 354 that exists, in at least some embodiments, owing to the relatively large output impedance of the microphone 354. This lowering of the noise is relative to that which would be the case in the absence of the amplifier. It is noted that in some alternate embodiments, the preamplifier 358 is part of the MEMS microphone 354. In an exemplary embodiment, an A/D converter is integrated in the sensor assembly 350.

In an exemplary embodiment, the microphone 354 (sensor) utilizes a so-called air back sensor. That said, in at least some exemplary embodiments, a so-called water backed sensor (or liquid backed sensor) can be utilized. Accordingly in an exemplary embodiment, the medium which fills the interior cavity of the apparatus 320 can be a liquid.

In an exemplary embodiment, the microphone is a MQM 31692 Knowles microphone.

It is further noted that in alternate embodiments, the microphone 354 can be a MEMS microphone of a different species than the condenser microphone. In an exemplary embodiment, any MEMS-based membrane type sensor can be utilized such as by way of example, a capacitive, an optical, a piezoelectric membrane type sensor etc. Further, in an alternate embodiment, the microphone 354 need not be MEMS based. Any device, system, and/or method, they can transducer the pressure changes inside the closed system of the apparatus 320 can be utilized in at least some embodiments, providing that the teachings detailed herein and/or variations thereof can be practiced.

The microphone 354 transduces the pressure variations and outputs the transduced energy via electrical lead 399. Via electrical lead 399, the output of the microphone is received by the receiver stimulator 180 of the cochlear implant 100. In some embodiments, the sound processor of the cochlear implant 100 (the sound processor is typically located in the receiver stimulator 180 or in an implantable sound processor housing remote from the receiver stimulator 180 but in signal communication with the stimulator 180) receives the output of the microphone 354 or signal indicative of the output of the microphone 354, and processes that output into a signal (including a plurality of signals) that are used by the stimulator 182 to formulate output signal to the electrode array of the electrode array assembly to electrically stimulate the cochlea and evoke a hearing percept. In the exemplary embodiment as just described, the electrode array assembly 390 is utilized in a so-called totally implantable hearing prosthesis. Thus, in an exemplary embodiment, there is a method of evoking a hearing percept by electrically stimulating the cochlea based on a physical phenomenon within the cochlea, where, in at least some embodiments, the method is executed without intervening input from a component outside the recipient (i.e. no intervening input between the physical phenomenon within the cochlea and the stimulation of the cochlea). Alternatively, in an alternate exemplary embodiment, a signal indicative of the sensed physical phenomenon within the cochlea is outputted to an external component of the hearing prosthesis, which includes a sound processor, which sound processor processes the signal into a signal that is then transcutaneously transmitted to the receiver stimulator 180 inside the recipient where the receiver stimulator 180 utilizes that signal to output a signal to the electrode array of the electrode array assembly to electrically stimulate the cochlea and evoke a hearing percept. Additional details of such exemplary methods and systems and devices to execute such methods are detailed further below.

Figure 6:
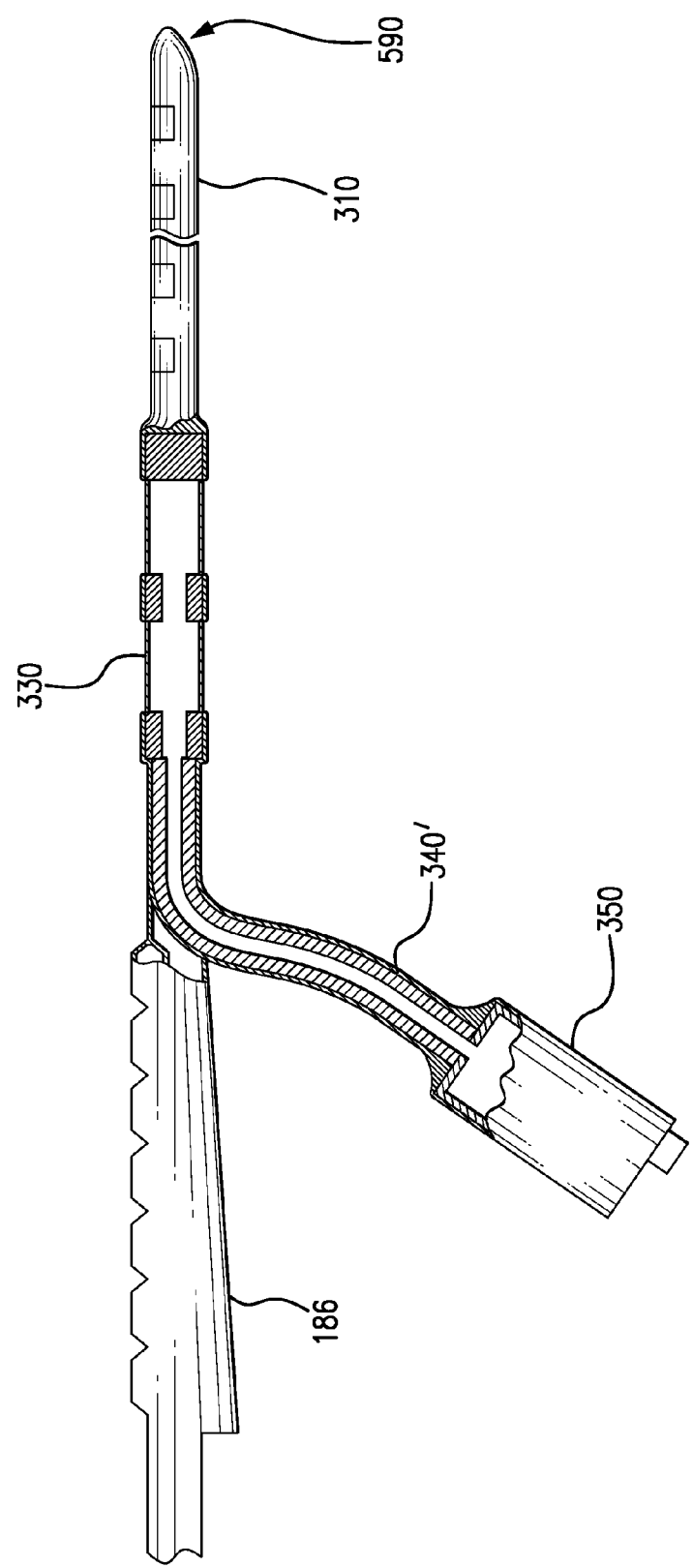
FIG. 6 is a side view of an alternate embodiment of a cochlear implant electrode array.

FIG. 6 depicts an alternate embodiment in which the sensor assembly 350 is a separate unit from the electrode array assembly. More specifically, FIG. 6 depicts an electrode array assembly 590 which includes electrode array 310 and receptor 330. However, sensor assembly 350 is a remote separate unit from the electrode array assembly 590, albeit in fluid and pressure communication with the receptor 330 via conduit 340'. Thus, in contrasting the embodiment of FIG. 5 from the embodiment of FIG. 3A, it can be seen that in the embodiment of FIG. 3A, the apparatus 320 and the electrode array 310 are a single unit (i.e., the electrode array assembly 390 is a combined electrode array 310 and the apparatus 320). This is as differentiated from, for example, an electrode array assembly 190 to which, by way of example, one or more or all the components of the apparatus 320 are merely attached or otherwise linked to in a non-unitized manner, such as is the case with respect to the embodiment of FIG. 6, where the apparatus which will correspond to apparatus 320 of the embodiment of FIG. 3A includes portions which are part of the unit of the electrode array assembly 590 and portions which are not part of the unit of the electrode array assembly 590. In the exemplary embodiment of FIG. 3A, the structure of the electrode array assembly 390 is such that the apparatus 320 is an integral part of the electrode array assembly 390, just as is the case with the electrode array 310.

Figure 7A:
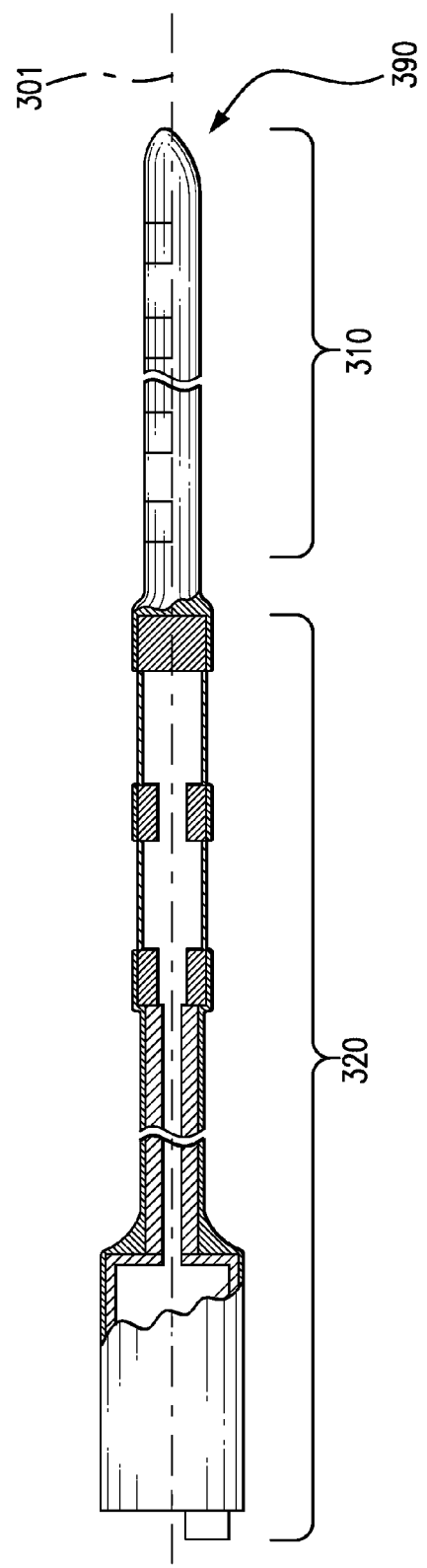
FIGS. 7A and 7B are side views of the embodiment of FIG. 3A.

Further, referring now to FIG. 7A, which corresponds the embodiment of FIG. 3A, the electrode array assembly 390 is configured such that the apparatus 320 is fixed relative to position along the longitudinal axis 301, where the longitudinal axis extends through the electrode array. This embodiment is in contrast to the embodiment of FIG. 6, where the conduit 340' enables sensor assembly 350 to move relative to position along the longitudinal axis of the electrode array assembly 590. Moreover, with respect to the embodiment of FIG. 3A (and thus FIG. 6), the outer profile of the electrode array 310 and the apparatus 320 are substantially coaxial with the longitudinal axis 301, as can be seen.

As can be seen from the figures, the electrode array assembly 390 includes a layer of silicone 302 covering the sensor assembly 350, the conduit 340, portions of the receptor 330, as well as portions of the electrode array 310, although with regard to the latter, a substantial amount of the electrode array 310 is made of silicone. The areas over the diaphragms 334 are not covered by silicone, at least in some exemplary embodiments. In an exemplary embodiment, silicone is not provided over the diaphragms 334 so as to avoid the potential of the silicone dampening the effect of the pressure waves on the diaphragms and/or increasing the stiffness of the diaphragm and hence reducing the sensitivity of the receptor. Accordingly, with respect to the embodiments of the figures, there is an electrode array assembly 390 that includes the apparatus 320 and the electrode array 310 that is substantially entirely covered by silicone. With respect to the embodiments of the figures, the electrode array assembly is so covered without any breaks or segments in the silicone, save for the working components of the electrode array assembly 390 (e.g., diaphragms 334, electrodes 148, etc.). This is distinguished from an embodiment where, for example, the sensor assembly is a separate unit from the electrode array assembly having its own covering of silicone which stops the boundary of that separate unit. Accordingly, an exemplary embodiment includes an electrode array assembly 390 that has a silicone covering that does not include any seams corresponding to separate applications of silicone (e.g., the silicone covering the electrode array assembly was deposited thereon in one manufacturing action).

The embodiment of FIG. 3A is such that movement of the cochlear implant electrode array in the longitudinal direction relative to the longitudinal axis thereof necessarily results in a corresponding movement of all and/or part of the apparatus 320 of at least substantially equal magnitude in the same direction. In this regard, during insertion of the intra-cochlea region 188 of the electrode array assembly 390 into the cochlea, which corresponds to movement of the electrode array assembly in the longitudinal direction relative to the longitudinal axis (irrespective of the fact that at least a portion of the intra-cochlea region 188 in general, and the electrode array 310 in particular, adopts a spiral configuration as it winds its way along the cochlea) the sensor assembly 350, including the microphone 354, the conduit 340, and the receptor 330, all move in the longitudinal direction by at least substantially the same amount in the same direction. This as compared to the embodiment of FIG. 6, at least where the conduit 340' is a flexible conduit.

Figure 7B:
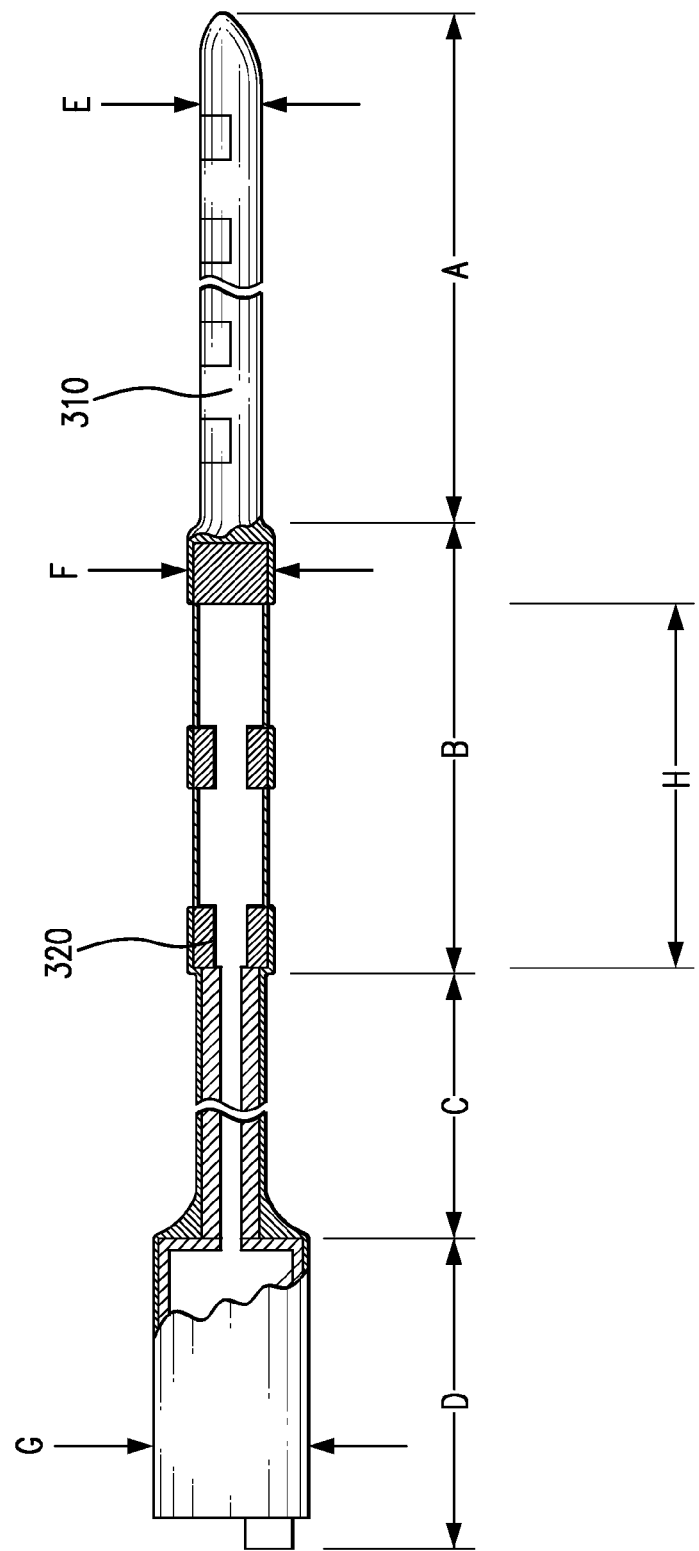

FIG. 7B depicts some exemplary dimensions of the exemplary embodiment of FIG. 3A. Unless otherwise specified, all dimensions are in millimeters. Dimension A can be about 5, 6, 7, 8, 9, 10, 11, 12, 13, 14, 15, 16, 17, 18, 19, 20, 21, 22, 23, 24, 25 or more or any value or range of values therebetween in about 0.1 mm increments (e.g., about 6.5 to about 17.3 mm, 11.3 mm, 20.4 mm, etc.). Dimension B can be about 0.5, 0.6, 0.7, 0.8, 0.9, 1.0. 1.1, 1.2, 1.3, 1.4, 1.5, 1.6, 1.7, 1.8, 1.9, 2.0, 2.1, 2.2, 2.3, 2.4, 2.5 or more or any value or range of values therebetween in about 0.05 mm increments (e.g., about 0.65 to about 1.56 mm, etc.). Dimension C can be about 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10 or more or any value or range of values therebetween in about 0.1 mm increments. Dimension D can be about 0.5, 0.6, 0.7, 0.8, 0.9, 1.0. 1.1, 1.2, 1.3, 1.4, 1.5, 1.6, 1.7, 1.8, 1.9, 2.0, 2.1, 2.2, 2.3, 2.4, 2.5, 2.6. 2.7, 2.8, 2.9, 3.0, 3.1, 3.2, 3.3, 3.4, 3.5, 3.6, 3.7, 3.8, 3.9, 4.0 or more or any value or range of values therebetween in about 0.05 mm increments (e.g., about 1.65 mm to about 2.56 mm, etc.). Dimension E can be about 0.1, 0.2, 0.3, 0.4, 0.5, 0.6, 0.7, 0.8, 0.9, 1.0. 1.1, 1.2, 1.3, 1.4, 1.5 or more or any value or range of values therebetween in about 0.01 mm increments (e.g., about 0.22 to about 0.54 mm, etc.). Dimension F can be about 0.3, 0.4, 0.5, 0.6, 0.7, 0.8, 0.9, 1.0. 1.1, 1.2, 1.3, 1.4, 1.5, 1.6, 1.7, 1.8, 1.9, 2.0, 2.1, 2.2, 2.3, 2.4, 2.5 or more or any value or range of values therebetween in about 0.05 mm increments (e.g., about 0.25 to about 0.75 mm, etc.). Dimension G can be about 1.0. 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 or more or any value or range of values therebetween in about 0.05 mm increments (e.g., about 0.65 to about 1.56 mm, etc.). Dimension H, which corresponds to the length of the internal space of the receptor can be about 0.4, 0.5, 0.6, 0.7, 0.8, 0.9, 1.0. 1.1, 1.2, 1.3, 1.4, 1.5, 1.6, 1.7, 1.8, 1.9, 2.0, 2.1, 2.2, 2.3 or more or any value or range of values therebetween in about 0.05 mm increments (e.g., about 0.65 to about 1.56 mm, etc.). It is further noted that in some embodiments, the components of the sensor assembly 350 are to scale. In an exemplary embodiment, the electrode array 390 is configured such that after insertion into the cochlea, there is about a 3.5, 4, 4.5, 5, 5.5, 6, or 6.5 mm or more or any value or range of values therebetween in 0.1 mm increments between the round window and the beginning of the electrodes of the electrode array 310. In an exemplary embodiment, the electrode array 390 is configured such that after insertion into the cochlea, there is about a 1, 1.5, 2, 2.5, 3 or 3.5 mm or more or any value or range of values therebetween in 0.1 mm increments between the round window and the beginning of the receptor 330. In an exemplary embodiment, the interior volume of the sound receptor is about 0.20, 0.25, 0.3, 0.35, 0.4, 0.45, 0.5, 0.55, 0.6, 0.65 $mm^3$ or more or any value or range of values therebetween in 0.01 $mm^3$ increments. In an exemplary embodiment, the internal diameter of the receptor 330 is about 0.4, 0.45, 0.5, 0.55, 0.6, 0.65, 0.7, 0.75 or 0.8 mm or any value or range of values therebetween in 0.01 mm increments. In an exemplary embodiment, the interior volume of the conduit about 0.7, 0.75, 0.8, 0.85, 0.9, 0.95, 1.0, 1.05, 1.1, 1.15, 1.2, 1.25 mm$^3$ or more or any value or range of values therebetween in 0.01 mm$^3$ increments. In an exemplary embodiment, the interior volume of the sensor assembly 350 is about 10, 11, 12, 13, 14, 15, 16, 17, 18, 19, 20, 21, 22 mm$^3$ or more or any value or range of values therebetween in 0.01 mm$^3$ increments.

In view of the above, it can be seen that in at least some embodiments, consistent with the embodiment of FIG. 3B, the microphone 354 (sensor/transducer) is located at least substantially immediately proximate to the base of the cochlea 140 outside the cochlea 140.

In an exemplary embodiment, the apparatus 320, or at least the electrode array assembly 390 in general, is configured to effectively equalize (which includes equalize) the pressure inside the apparatus 320 with the pressure inside the middle ear of the recipient.

Some exemplary functionality characteristics of the apparatus 320 will now be described.

As noted above, the apparatus 320 is configured to sense a phenomenon of fluid in a cochlea. The phenomenon can be a pressure, a pressure change, vibratory energy, or any phenomenon that can enable the teachings detailed herein and/or variations thereof to be practiced. According to at least some exemplary embodiments, the phenomenon that is sensed is a phenomenon that results from exposure of a recipient to a sound (acoustic energy, and thus the physical phenomenon is energy originating from acoustic energy), where this sound causes a change in a physical property of the fluid inside the cochlea. The receptor 330 is configured such that a physical property of the receptor, and thus the apparatus 320, changes as a result of the phenomenon in the fluid in the cochlea (the change in the physical property within the fluid of the cochlea). In particular, with respect to the embodiment of FIG. 3A, the phenomenon causes the diaphragms 334 to deform (move), and this movement causes the pressure variation within the receptor 334, and thus the enclosed volume within the apparatus 320, to fluctuate. Thus, a physical property of the receptor (pressure) changes as a result of the phenomenon in the fluid. Thus, the receptor 330 effectively receives the phenomenon. It is noted that this is the case to irrespective of whether the physical phenomenon is pressure/pressure change and/or vibrational energy, etc.

As noted above, with respect to FIG. 3B, a portion of the apparatus 320 extends from inside the cochlea to outside the cochlea. More particularly, the closed volume of the apparatus 320 extends from inside the cochlea to outside the cochlea. Thus, when the receptor 330 receives the physical phenomenon within the cochlea of the fluid, and the diaphragms 334 are deflected or otherwise moved as a result, the physical phenomenon indicative of a change in the physical property of the fluid is communicated from inside the cochlea to outside the cochlea. More particularly, the physical phenomenon is communicated from inside the cochlea, through conduit 340, to sensor assembly 350 and thus microphone 354 (sensor/transducer), which are thus located outside the cochlea. By way of example only and not by way of limitation, if a variation in pressure inside the cochlea causes the diaphragms to deflect or otherwise move, the deflection/movement of the diaphragms causes the internal pressure inside the receptor 330 to change. In embodiments where the internal portions of the apparatus 320 are filled with a gas or the like, this change in the internal pressure in the receptor 330 is fluidically communicated to the microphone 354 via conduit 340 and the pertinent portions of the sensor assembly 350. In embodiments where the apparatus 320 establishes a closed volume comprising the interior of the receptor 334, the interior of the conduit 340, and the interior of the sensor assembly 350, the communication is established by a closed volume which extends from the intra-cochlear sub-section to the middle-ear cavity sub-section of the electrode array assembly 390. As noted above, this closed volume is hermetically isolated from the environment in which the electrode array assembly 390 is utilized (e.g. cochlear fluid, the gas of the middle ear cavity (humid air), etc.). Because this closed volume extends from the intra-cochlear section to the proximal region section of the electrode array assembly 390, any changes of the physical property of the apparatus (e.g., pressure within the apparatus 320) that occur within this close volume occur in both sections of the electrode array assembly 390. In embodiments where the interior of the receptor 330, conduit 340, and sensor assembly 350 are full of gas, such as an inert gas (e.g. argon, etc.), indications of the changes/physical phenomenon are communicated via this fluid (gas). Thus in an exemplary embodiment, the changes are communicated from inside the cochlea to outside the cochlea without transduction (i.e., the use of a transducer). In an exemplary embodiment, the communicated physical phenomenon is the same as the physical phenomenon corresponding to the change in the physical property of the fluid.

In at least some exemplary embodiments, the apparatus 320 is configured such that the acoustic sensitivity of the apparatus is greater than and/or equal to about −35, −40, −45, −50, −55, −60 dB V/Pa or any value or range of values therebetween in 1 dB V/Pa increments, when receiving pressure waves resulting from sound between, for example, 100 Hz and 6 kHz that change the physical property of the fluid inside the cochlea. Still further, in at least some exemplary embodiments, the apparatus 320 is configured such that the equivalent input noise of the apparatus is no more than and/or equal to about 15, 20, 25, 30, 35, 40, 45, 50 or 55 dB SPL or any value or range of values therebetween in 1 dB increments, when receiving pressure waves resulting from sound between 100 Hz and 6 kHz, and/or 1.5 kHz and 7 kHz that change the physical property of the fluid. In an exemplary embodiment, the aforementioned values are entirely attributable to the sensor/microphone 350 of the apparatus, while in other embodiments, the aforementioned values are attributable to a combination of the elements of the apparatus 320.

Figure 7C:
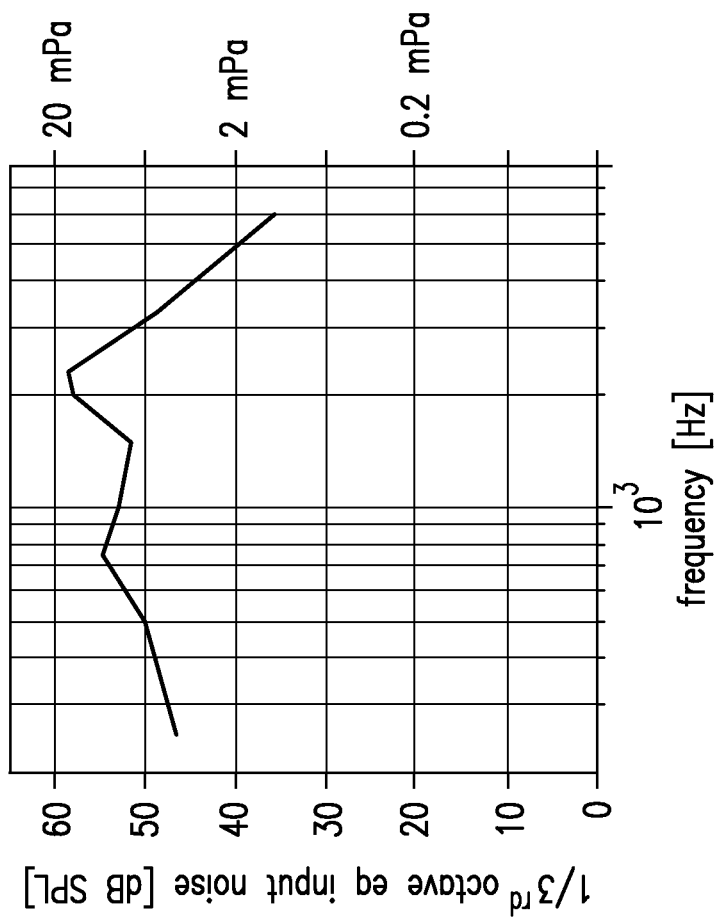
FIG. 7C depicts a graph depicting an exemplary functionality of an exemplary electrode array assembly according to an exemplary embodiment.

In an exemplary embodiment, the equivalent input noise of the apparatus utilizing the exemplary electrode array assembly according to the teachings detailed herein and/or variations thereof has a value corresponding to values below the curve presented in FIG. 7C, at least in embodiments where the recipient of the electrode array assembly has 30 dB hearing loss.

Still further, it is noted that in at least some embodiments, a power consumption of the apparatus 320 (e.g. the power consumed by the microphone 354) when operating according to the teachings detailed herein and/or variations thereof (e.g., to transduce the physical phenomenon and provide the signal to the sound processor) is less than about 1 mW, 0.9, 0.8, 0.7, 0.6, 0.5, 0.4, 0.3, 0.2, 0.1 mW, 90 µW, 80 µW, 70 µW, 60 µW, 50 µW, 40 µW, 30 µW, 20 µW, 10 µW or less or any value or range of values therebetween in 0.1 µW, increments.

Some exemplary methods will now be described. It is noted at this time that some embodiments include any method action that results from use of the devices and systems disclosed herein and or variations thereof. That is, any disclosure of a device or system herein also corresponds to a disclosure of utilizing that device, such as utilization of that device in accordance with the teachings detailed herein and or variations thereof to evoke a hearing percept. It is further noted at this time that some embodiments include any device or system that has the functionality of executing any method action detailed herein and/or variations thereof. That is any disclosure of a method or method action or system herein also corresponds to a disclosure of a device and/or system having the functionality to execute that method action (and/or the entire method).

Figure 8:
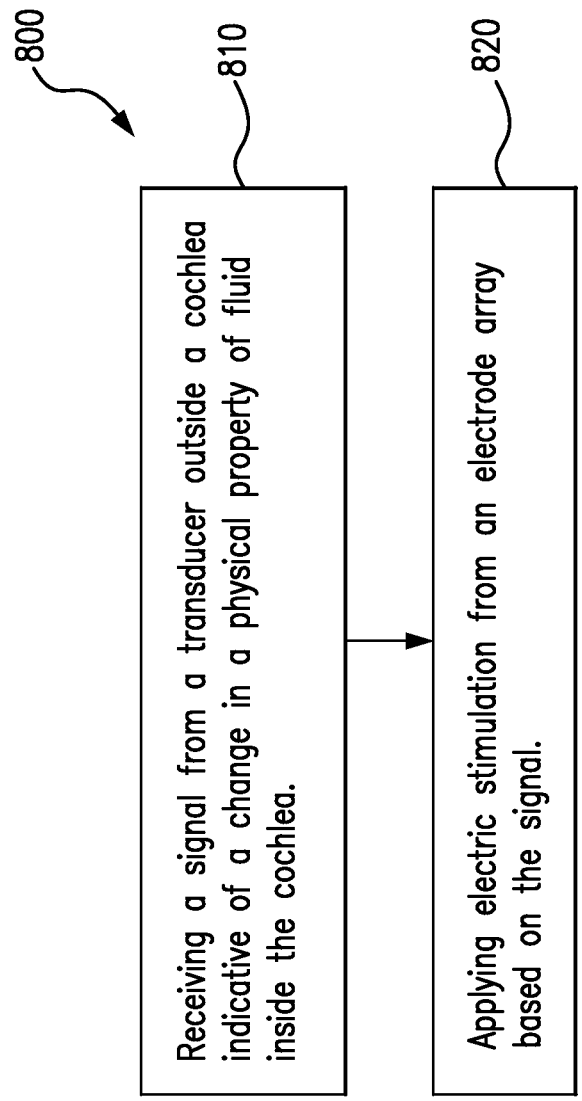
FIGS. 8 and 9 depict exemplary flowcharts for exemplary methods according to some exemplary embodiments.
Figure 9:
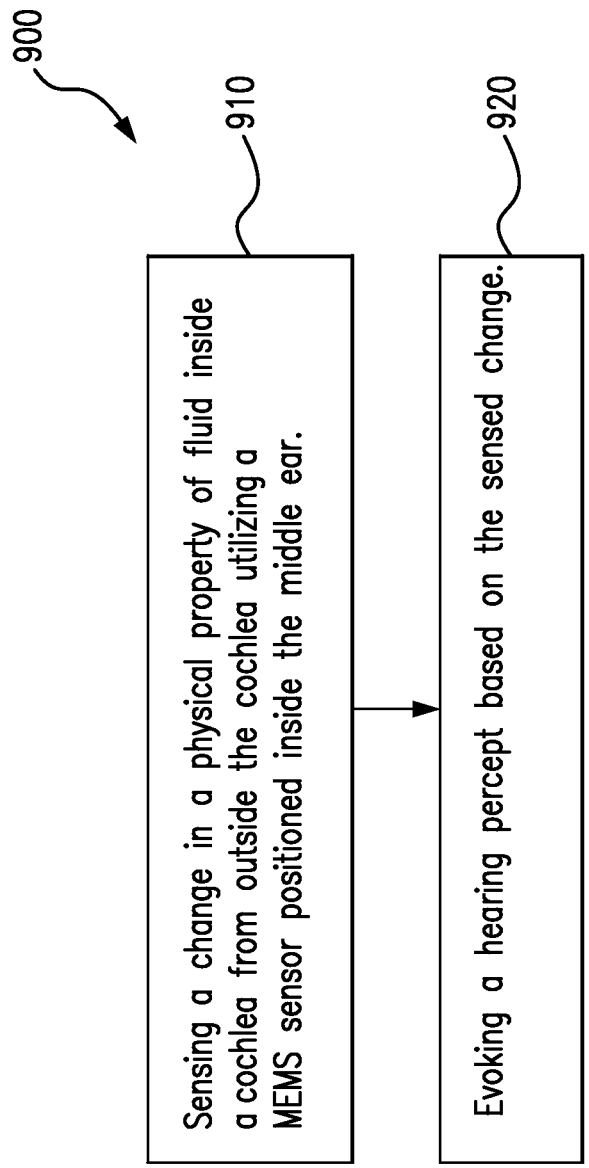

Referring now to FIG. 8, a flowchart 800 for an exemplary method is presented. In an exemplary embodiment, there is a cochlear implant, such as cochlear implant 100, that is configured to execute this method automatically. In an exemplary embodiment, this exemplary cochlear implant 100 includes the electrode assembly 118 that includes electrode array assembly 390. Flowchart 800 includes method action 810, which entails receiving a signal, such as the output from the lead to 399 from sensor apparatus 350, from a transducer (e.g., a pressure sensitive transducer), such as microphone 354. Method action 810 is executed when the transducer is located at least substantially immediately proximate to the base of a cochlea outside the cochlea, such as is the case in the exemplary schematic of FIG. 3B. Method action 810 also entails executing that action such that the signal is indicative of a change in a physical property of fluid inside the cochlea, such as can be the case when the recipient of the cochlear implant 100 is exposed to sound and acoustic energy from that sound causes a change in the physical property of the fluid inside the cochlea as detailed herein. Flowchart 800 further includes method action 820, which entails applying electric stimulation from a cochlear implant electrode array, such as the electrode array 310 of electrode array assembly 390, to the cochlea, based on the signal from the transducer. In an exemplary embodiment, this electric stimulation evokes a hearing percept.

In accordance with the embodiments detailed above, the exemplary method can include the action of communicating a physical phenomenon indicative of a change in a physical property of the fluid inside the cochlea to the sensor outside the cochlea. Also in accordance with the embodiments detailed herein, in some exemplary methods, the communicated physical phenomenon is the same as the physical phenomenon corresponding to the change in the physical property.

As noted above, the change in the physical property of the fluid inside the cochlea results from the exposure the recipient to a sound. In an exemplary embodiment, the sound exposed to the recipient has a wavelength. In an exemplary method, the communication of the physical phenomenon indicative of the change in the physical property from inside the cochlea to the sensor takes place all over a distance no more than about an order of magnitude smaller than the wavelength of the sound to which the recipient is exposed. For example, in a scenario where the sound has a wavelength of 85 mm, the communication distance is no more than about 8.5 mm. In this regard, referring to FIG. 7B, the distance from the rightmost interior portion of the receptor 330 to the microphone 354 would thus be no more than about 8.5 mm. That said, in alternative embodiments, there is a method where the distance of communication is no more than about an order of magnitude smaller than 0.7, 0.8, 0.9, 1.1, 1.2 or 1.3 times the wavelength of the sound.

Further along these lines, there is a method that entails inserting a cochlear implant electrode array assembly into a cochlea. The electrode array assembly includes a transducer and a receptor, although the transducer is not inserted into the cochlea. The electrode array assembly is inserted into the cochlea such that a working element of the receptor or (e.g. diaphragm 334) is located within about 4 mm from the round window of the cochlea. In an exemplary embodiment, all of the working elements of the receptor are located within about 4 mm from the round window of the cochlea. In an exemplary embodiment, one or more or all of the working elements of the receptor are located within about 10 mm, 9.5 mm, 9.0 mm, 8.5 mm, 8.0 mm, 7.5 mm, 7.0 mm, 6.5 mm, 6.0 mm, 5.5 mm, 5.0 mm, 4.5 mm, 4.0 mm, 3.5 mm, 3.00 mm or less or any value therebetween in 0.1 mm increments from the round window the cochlea. It is further noted that in an exemplary embodiment includes a method of operating or otherwise utilizing such an implanted cochlear electrode array.

Still further, in accordance with the teachings detailed herein and/or variations thereof, the method of flowchart 800 further comprise the action of exposing a recipient to the sound, where the sound directly or indirectly causes a wave to travel along the length of the cochlea. This changes the physical property of the fluid inside the cochlea. The method further includes receiving energy from the wave via a diaphragm, such as diaphragms 334 of receptor 330 position inside the cochlea that are in fluid communication with the fluid inside the cochlea.

Another exemplary method entails inserting an electrode array assembly that includes a transducer into a cochlea of a recipient. The electrode array assembly is such that when this method action is executed, movement of the cochlear implant electrode array in the direction of insertion into the cochlea necessarily results in a corresponding movement of the transducer of at least substantially equal magnitude in that direction. In an exemplary embodiment, if the electrode array is moved forward into the cochlea a distance of 5 mm, the transducer is also moved 5 mm. In an exemplary embodiment, this method is achieved by utilizing the electrode array assembly 390 of the embodiment of FIG. 3A.

Accordingly in an exemplary method there is a surgical procedure which entails placement of the electrode array into the recipient simultaneously with placement of the apparatus 320 into the recipient. That is, placement of the electrode array also entails placement of the apparatus. In an exemplary embodiment, no additional actions are required to place the apparatus relative to that which is required to place the electrode array.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A device, comprising:
  a cochlear implant electrode array; and
  an apparatus configured to sense a phenomenon of fluid in a cochlea, wherein the apparatus and the electrode array are a single unit, wherein
  the apparatus includes a diaphragm that moves in response to exposure thereof to the phenomenon and a sensor with a component in fluid communication with the diaphragm; and
  the device is configured such that the component moves in response to a transfer of energy via the fluid communication with the diaphragm from external to the apparatus to internal to the apparatus upon the occurrence of the phenomenon, wherein the sensor outputs a signal in response to movement of the component.

2. The device of claim 1, wherein:
the apparatus is a pressure sensor assembly.
3. The device of claim 1, wherein:
the apparatus is configured such that a first physical property of the apparatus changes as a result of the phenomenon in the fluid, thereby effectively receiving the phenomenon of the fluid.
4. The device of claim 1, wherein:
the phenomenon is at least one of a change in pressure and a pressure of the fluid in the cochlea.
5. The device of claim 1, wherein:
the device has a longitudinal axis that extends through the electrode array; and
the apparatus is fixed relative to position along the longitudinal axis.
6. The device of claim 1, wherein:
the apparatus is configured such that a first physical property of the apparatus changes as a result of the phenomenon of the fluid in a cochlea, wherein the first physical property changes both an intra-cochlear section and a proximal region section of the cochlear implant electrode array assembly.
7. The device of claim 1, wherein:
the device is a cochlear implant electrode array assembly wherein the apparatus is an integral part of the electrode array assembly.
8. The device of claim 1, wherein:
the device has a first longitudinal axis that extends through the electrode array and through the apparatus, wherein an outer profile of the electrode array and the apparatus are substantially coaxial with the longitudinal axis.
9. The device of claim 1, wherein:
the apparatus is a transducer configured to convert mechanical energy to an electrical signal.
10. The device of claim 2, wherein:
the phenomenon is a pressure phenomenon; and
the apparatus is configured as a transducer configured to output an electrical signal indicative of the pressure phenomenon.
11. The device of claim 1, wherein:
the apparatus includes a transducer, the transducer being a condenser microphone.
12. The device of claim 1, wherein:
the apparatus includes a pre-amplifier.
13. The device of claim 1, wherein:
the apparatus is configured to transduce energy and output an electrical signal indicative of the sensed phenomenon.
14. The device of claim 1, wherein:
the apparatus includes a front volume and a back volume divided by a backplate.
15. The device of claim 2, wherein:
the apparatus establishes a completely enclosed volume in which a fluid is located, the fluid being configured to transmit pressure changes from a first end of the enclosed volume to a second end of the enclosed volume located most distant from the first end.
16. The device of claim 1, wherein:
the apparatus includes a microphone that is in fluid communication with the diaphragm, which diaphragm is exposed to the fluid of the cochlea so as to move in response to the phenomenon, wherein energy resulting from movement of the diaphragm is fluidically conducted to the microphone.
17. The device of claim 1, wherein:
the apparatus is a cochlear microphone apparatus.
18. A device, comprising:
a cochlear implant electrode array; and
an apparatus configured to sense a phenomenon of fluid in a cochlea, wherein the apparatus and the electrode array are a single unit, wherein
at least one of:
(i) the apparatus includes a receptor configured to receive the phenomenon of fluid in the cochlea; and
the apparatus also includes a sensor remote from the receptor, wherein the device is configured such that the phenomenon received by the receptor is communicated without transduction to the sensor remote from the receptor; or
(ii) the apparatus includes a diaphragm configured to receive the phenomenon of fluid in the cochlea; and
the apparatus also includes a sensor remote from the diaphragm, wherein the device is configured such that the phenomenon received by the diaphragm is communicated without transduction to the sensor remote from the diaphragm.
19. The device of claim 18, wherein:
the apparatus includes the diaphragm configured to receive the phenomenon of fluid in the cochlea; and
the apparatus also includes the sensor remote from the diaphragm, wherein the device is configured such that the phenomenon received by the diaphragm is communicated without transduction to the sensor.
20. The device of claim 18, wherein:
the apparatus includes the receptor configured to receive the phenomenon of fluid in the cochlea; and
the apparatus also includes the sensor remote from the receptor, wherein the device is configured such that the phenomenon received by the receptor is communicated without transduction to the sensor remote from the receptor.
21. A device, comprising:
a cochlear implant electrode array; and
an apparatus configured to sense a phenomenon of fluid in a cochlea and output a signal indicative of the sensed phenomenon, wherein
the apparatus and the electrode array are a single unit, wherein
the device is configured to receive, at a first location, the phenomenon of fluid in the cochlea, wherein the first location is a location that is inside the cochlea when the cochlear implant electrode array is fully inserted into a cochlea, and
the apparatus also includes a sensor remote from the first location, wherein the device is configured such that the sensor is in fluid communication with the first location via a conduit wherein the first location includes a diaphragm that moves in response to exposure thereof to the phenomenon.
22. The device according to claim 21, wherein:
the apparatus includes a physical phenomenon receptor and a sensor remote from the receptor, the sensor being configured to output the signal indicative of the sensed phenomenon;
the device is configured such that the physical phenomenon received by the receptor is communicated to the sensor; and
the apparatus and the electrode array are a single unit.

23. The device according to claim 21, wherein:
the device is configured such that the phenomenon received at the first location is in an energy form that is the same as that received by the sensor.

24. A device, comprising:
a cochlear implant electrode array; and
an apparatus configured to sense a phenomenon of fluid in a cochlea, wherein the apparatus and the electrode array are a single unit, wherein
the phenomenon is a pressure phenomenon, and
the apparatus includes a diaphragm that moves in response to exposure thereof to the pressure phenomenon and includes a transducer having a component that moves that is in fluid communication with the diaphragm that outputs, via transduction, an electrical signal in response to movement of the diaphragm.

25. A device, comprising:
a cochlear implant electrode array including a component configured to move in response to a physical phenomenon within a cochlea; and
a middle-ear cavity sub-section including a sensor in fluid communication with the component configured to move in response to the physical phenomenon, wherein
the cochlear implant electrode array, the component configured to move in response to a physical phenomenon and the sensor are a single unit.

26. The device of claim 25, wherein:
the device configured to move in response to a physical phenomenon is a pressure receptor; and
the sensor is a pressure sensor.

* * * * *